US011660084B2

(12) United States Patent
Khalil et al.

(10) Patent No.: US 11,660,084 B2

(45) Date of Patent: May 30, 2023

(54) FASTENER ANCHORING DEVICE

(71) Applicant: AEVUMED, INC., Malvern, PA (US)

(72) Inventors: Saif Khalil, Malvern, PA (US); Miles Curtis, Philadelphia, PA (US); Eric Black, Livingston, NJ (US); Grant Edward Garrigues, Hinsdale, IL (US); Robert James Gillespie, Shaker Heights, OH (US); Anand Murugan Murthi, Lutherville, MD (US); Surena Namdari, Gladwyne, PA (US); Eric Jason Strauss, Scarsdale, NY (US)

(73) Assignee: AEVUMED, INC., Malvern, PA (US)

( * ) Notice: Subject to any disclaimer, the term of this patent is extended or adjusted under 35 U.S.C. 154(b) by 80 days.

(21) Appl. No.: 16/953,629

(22) Filed: Nov. 20, 2020

(65) Prior Publication Data

US 2021/0153861 A1 May 27, 2021

Related U.S. Application Data

(60) Provisional application No. 62/938,475, filed on Nov. 21, 2019.

(51) Int. Cl.

| | |
|---|---|
| ***A61B 17/04*** | (2006.01) |
| ***A61B 17/068*** | (2006.01) |
| ***A61B 17/062*** | (2006.01) |
| ***A61B 17/064*** | (2006.01) |
| ***A61B 17/00*** | (2006.01) |

(52) U.S. Cl.

CPC ........ *A61B 17/0401* (2013.01); *A61B 17/062* (2013.01); *A61B 17/068* (2013.01); *A61B 2017/00884* (2013.01); *A61B 2017/00893* (2013.01); *A61B 2017/0409* (2013.01); *A61B 2017/0412* (2013.01); *A61B 2017/0446* (2013.01); *A61B 2017/0464* (2013.01); *A61B 2017/0647* (2013.01)

(58) Field of Classification Search

CPC . A61B 17/0401; A61B 17/062; A61B 17/068; A61B 2017/00884; A61B 2017/00893; A61B 2017/0409; A61B 2017/0412; A61B 2017/0446; A61B 2017/0464; A61B 2017/0647; A61B 17/072; A61B 2017/00889; A61B 2017/0495; A61B 2017/07278; A61B 17/07292; A61B 17/0682; A61B 17/01; A61B 17/0686; A61B 17/105; A61B 17/11; A61B 17/115; A61B 17/0487; A61B 17/0491; A61B 2017/1125; A61B 2017/0488; A01K 11/00; A01K 11/001; A01K 11/002; A01K 11/003; A01K 13/003; A01K 17/01285; A01K 17/0128; A01K 17/07207

See application file for complete search history.

(56) References Cited

U.S. PATENT DOCUMENTS

2019/0343518 A1* 11/2019 Shelton, IV .......... B25C 5/0292

* cited by examiner

*Primary Examiner* — Shaun L David

*Assistant Examiner* — Rachael L Geiger

(74) *Attorney, Agent, or Firm* — Riverside Law LLP

(57) ABSTRACT

The present invention provides fastener anchoring devices with protruding fasteners releasably attached to graspers for insertion into a target site such as soft tissue. The devices include a retaining mechanism that can be actuated to release the fasteners from the grasper. The devices can include support material preloaded onto the fasteners.

18 Claims, 4 Drawing Sheets

100 120 106 122 112 118 116 104 102 124 108

120 106 122 112 118 116 104 102 124 108

FASTENER ANCHORING DEVICE

CROSS REFERENCE TO RELATED APPLICATIONS

This application claims priority to U.S. Provisional Application No. 62/938,475, filed Nov. 21, 2019 which is hereby incorporated by reference herein in its entirety.

BACKGROUND OF THE INVENTION

Soft tissue tears are common and many repair methods rely solely on the mechanical attributes of fasteners to repair the soft tissue. However, the fasteners alone are inadequate for proper healing, as the soft tissue is in a weakened state and penetrating the soft tissue with the fasteners merely introduces additional weak points that are prone to further tearing. Furthermore, commonly used fastener applicators present smooth jaw clamping surfaces with recessed fasteners that provide inadequate grip on soft tissue, necessitating excessive clamping force on soft tissue to minimize slippage prior to fastener insertion.

Thus, there is a need in the art for improved tissue fastening devices that enhance repair and healing. The present invention meets this need.

SUMMARY OF THE INVENTION

In one aspect, the present invention relates to a fastener anchoring device, comprising: a shaft connected to a proximal handle and a distal grasper; wherein the grasper comprises an upper jaw connected to a lower jaw; wherein at least one of the upper jaw and lower jaw comprises at least one fastener slot adjacent to a channel having a slideable retaining band, the retaining band having a width that partially occludes the at least one fastener slot; and wherein a fastener having a fastener head is positioned in each fastener slot such that each fastener protrudes from each fastener slot and the retaining band holds each fastener head within each fastener slot.

In one embodiment, sliding the retaining band away from the at least one fastener slot releases the fastener positioned within the at least one fastener slot. In one embodiment, the retaining band comprises at least one release slot alignable with a fastener slot to complete an aperture sized to match a fastener head. In one embodiment, sliding the retaining band aligns the at least one release slot with the at least one fastener slot and releases the fastener positioned within the at least one fastener slot.

In one embodiment, the fastener is selected from the group consisting of: staples, barbs, pins, hooks, spurs, spikes, and anchors. In one embodiment, each fastener is biodegradable. In one embodiment, each fastener is non-biodegradable.

In one embodiment, a support material is preloaded onto at least one fastener protruding from the upper jaw, the lower jaw, or both. In one embodiment, the support material is a scaffold. In one embodiment, the support material is constructed from a synthetic material, a biological material, or both. In one embodiment, the support material comprises an anisotropic material. In one embodiment, the support material comprises an isotropic material.

In one embodiment, the synthetic material is selected from the group consisting of: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO), polyorthoesters, and combinations thereof.

In one embodiment, the biological material is selected from the group consisting of: collage, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g. cellulose and its derivatives), chitin, chitosan, alginic acids, alginates, and combinations thereof.

In one embodiment, the support material further comprises a factor selected from the group consisting of: epidermal growth factor (EGF), platelet derived growth factor (PDGF), basic fibroblast growth factor (bFGF), transforming growth factor-β (TGF-β), tissue inhibitors of metalloproteinases (TIMP), antibiotics, bacteriocides, fungicides, silver-containing agents, analgesics, nitric oxide releasing compounds, and combinations thereof.

In one embodiment, the support material further comprises a population of cells selected from the group consisting of: fibroblasts, osteoblasts, tenoblasts, tenocytes, ligament cells, keratinocytes, epithelial cells, endothelial cells, mesenchymal stem cells, embryonic stem cells, and combinations thereof.

In one embodiment, the upper jaw and the lower jaw are each laterally expandable. In one embodiment, a support material is preloaded onto at least one fastener protruding from the laterally expandable upper jaw, the laterally expandable lower jaw, or both.

In one embodiment, the device further comprises a retractable needle positioned in the upper jaw, the lower jaw, or both. In one embodiment, the retractable needle comprises a preloaded suture thread.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

The present invention provides fastener anchoring devices with protruding fasteners releasably attached to graspers for insertion into a target site such as soft tissue. The devices include a retaining mechanism that can be actuated to release the fasteners from the grasper. The devices can include support material preloaded onto the fasteners.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Fastener Anchoring Device

Figure 1A:
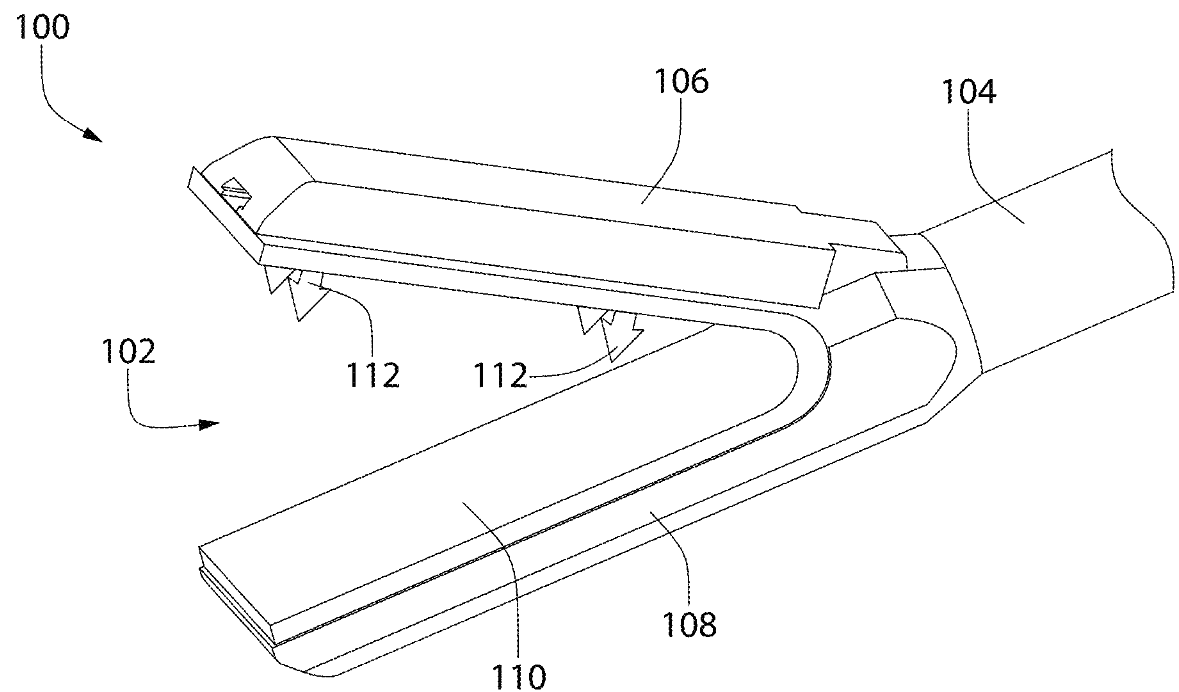
FIG. 1A depicts a magnified perspective view of a grasping end of an exemplary fastener anchoring device.
Figure 1B:
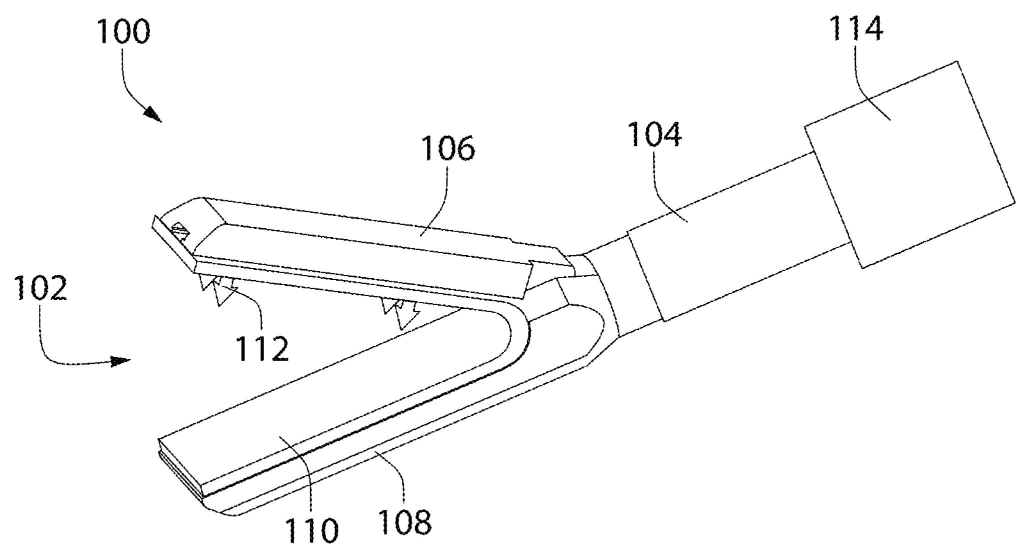
FIG. 1B depicts the same device as FIG. 1A but showing the handle.

Referring now to FIG. 1 and FIG. 1A, an exemplary fastener anchoring device 100 is depicted. Device 100 comprises a grasper 102 positioned at a distal end of shaft 104 and a handle 114 positioned at a proximal end of shaft 104. Shaft 104 can have any suitable length, shape, and diameter. For example, for laparoscopic use, shaft 104 can have a length between about 10 cm and 100 cm and a diameter sized to fit within a laparoscopic port. For non-laparoscopic use, shaft 104 can have a length between about 1 cm and 10 cm. Grasper 102 comprises upper jaw 106 connected to lower jaw 108, wherein upper jaw 106 and lower jaw 108 are actuated by a mechanical or electronic link extending to the handle 114 of device 100 via shaft 104. In some embodiments, upper jaw 106 and lower jaw 108 are each actuatable. In other embodiments, one jaw is actuatable while the opposing jaw is stationary. Upper jaw 106 and lower jaw 108 can be joined by any suitable connection, including but not limited to hinged connections and clamp connections. Upper jaw 106 and lower jaw 108 can be actuated around a pivot point, such as a hinged connection, or be actuated while in substantially parallel alignment, such as a bar clamp.

Figure 2:
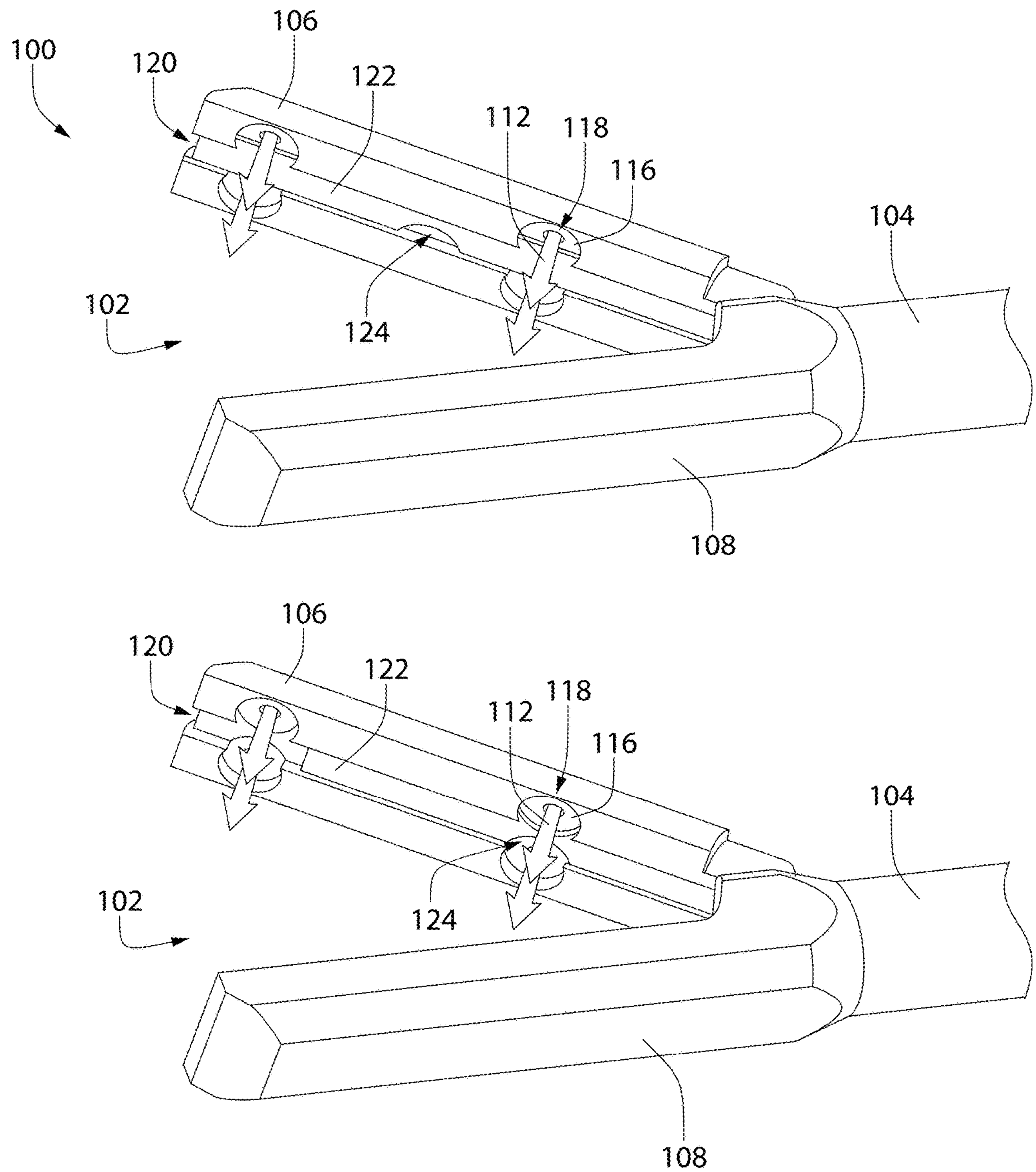
FIG. 2 depicts magnified perspective views of a grasping end of an exemplary fastener anchoring device in a locked configuration (top) and an unlocked configuration (bottom).

Visible in FIG. 2, grasper 102 comprises at least one fastener 112 positioned on upper jaw 106, lower jaw 108, or both. In some embodiments, grasper 102 comprises at least one array of fasteners 112. Each fastener 112 comprises a fastener head 116 sized to fit within a fastener slot 118 on upper jaw 106, lower jaw 108, or both. While fastener 112 is depicted as a tack having a circular fastener head 116, it should be understood that fastener 112 and fastener head 116 can have any form and shape with a pointed end suitable for piercing tissue. Contemplated fasteners 112 include but are not limited to staples, barbs, pins, hooks, spurs, spikes, anchors, and the like. Fasteners 112 can be biodegradable or non-biodegradable. In some embodiments, the array of fasteners 112 are retained within grasper 102 with piercing ends of each fastener 112 exposed.

Grasper 102 further comprises a channel 120 housing retaining band 122 in upper jaw 106, lower jaw 108, or both. Retaining band 122 is slidable within channel 120 and comprises a width that obstructs adjacent fastener slots 118 such that fastener head 116 of each fastener 112 is unable to exit each fastener slot 118, as depicted in the top image of FIG. 2. Each retaining band 122 is actuated by a mechanical or electronic link extending to the handle 114 of device 100 via shaft 104. Sliding a retaining band 122 within a channel 120 removes the width of retaining band 122 from adjacent fastener slots 118 to release fastener heads 116 held within. In some embodiments, each retaining band 122 comprises a plurality of release slots 124, wherein each release slot 124 is alignable with a fastener slot 118 to complete an aperture sized to match a fastener head 116, thereby releasing fastener heads 116 from the fastener slots 118.

Figure 3:
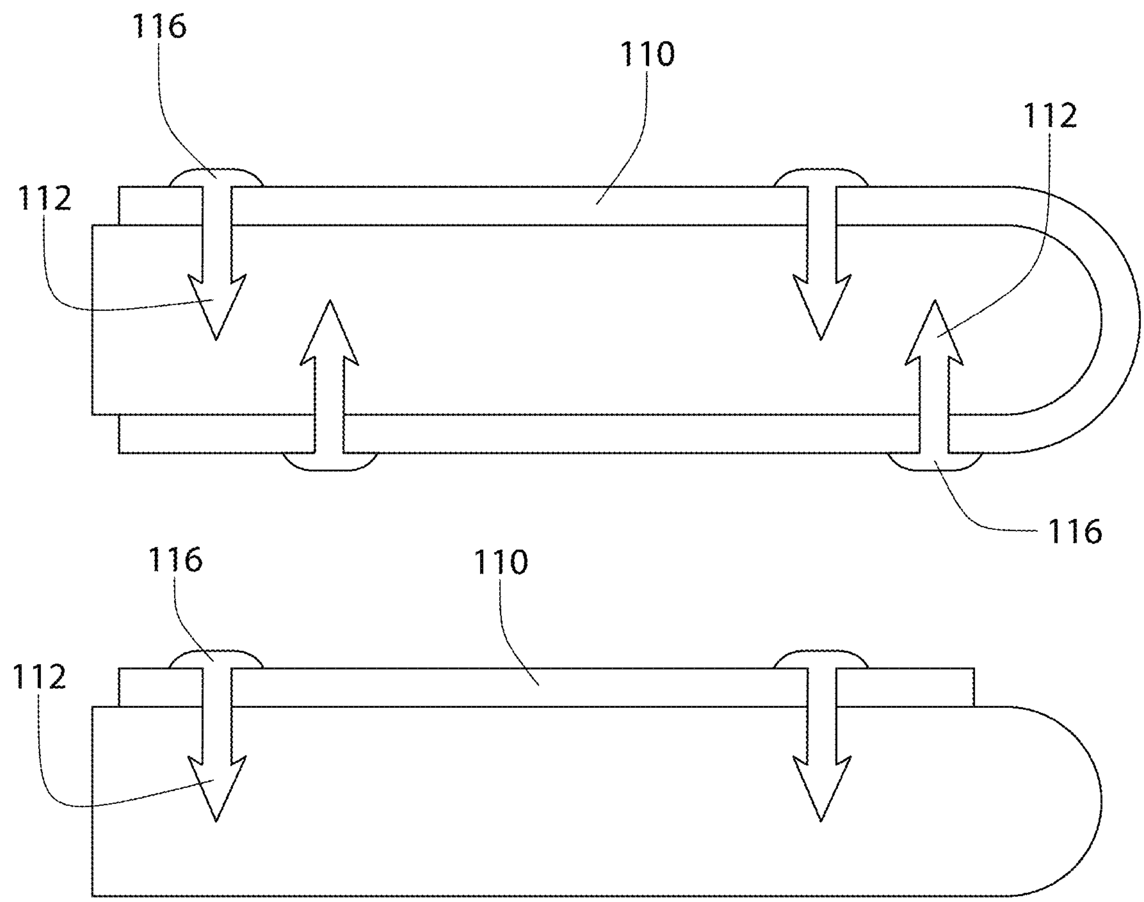
FIG. 3 depicts cross-sectional side views of fasteners and biomaterials anchored to soft tissue.

In various embodiments, a support material 110 can be preloaded onto fastener 112 arrays of grasper 102 for delivery to a target site. Support material 110 can have any desired shape, including but not limited to square, rectangular, polygonal, circular, ovoid, and irregularly shaped sheets. Support material 110 can comprise a single section loaded to upper jaw 106, lower jaw 108, or both. Support material 110 that is loaded onto both upper jaw 106 and lower jaw 108 can comprise two sections attached separately to each jaw, or a single section that folds from upper jaw 106 to lower jaw 108 (as depicted in FIG. 1). As shown in FIG. 3, grasper 102 is configured to deliver and fasten a support material 110 to a target site, such as to soft tissue. Grasping a target site with grasper 102 embeds each fastener 112 into the target site. Each fastener 112 may be released from grasper 102 by actuating retaining band 122 as described elsewhere herein, leaving behind support material 110 attached to the target site by fasteners 112 and fastener heads 116.

Support material 110 can be used to heal or repair a target site. For example, support material 110 can be used to wrap around a soft tissue such as a tendon or ligament for secure attachment to a bone surface. Support material 110 can comprise synthetic materials, biological materials, and combinations thereof to enhance biocompatibility and healing. Contemplated synthetic materials include but are not limited to: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Contemplated biological materials include but are not limited to: collagen (e.g. Type I with Type II, Type I with Type III, Type II with Type III, etc.), fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g. cellulose and its derivatives), chitin, chitosan, alginic acids, and alginates such as calcium alginate and sodium alginate.

In some embodiments, the biological materials are scaffolds. In some embodiments, the biological materials are tissue grafts. In some embodiments, support material 110 comprises isotropic materials. In other embodiments, support material 110 comprises anisotropic fibers, such that support material 110 can be positioned in a direction that aligns anisotropic fibers in a direction of natural or expected anatomic forces to resist tearing and further damage.

In various embodiments, support material 110 can be embedded or conjugated with factors that promote healing, including but not limited to epidermal growth factor (EGF), platelet derived growth factor (PDGF), basic fibroblast growth factor (bFGF), transforming growth factor-β (TGF-β), and tissue inhibitors of metalloproteinases (TIMP). Additional factors can include antibiotics, bacteriocides, fungicides, silver-containing agents, analgesics, and nitric oxide releasing compounds. Support material 110 may also be seeded with cells, such as fibroblasts, osteoblasts, tenoblasts, tenocytes, ligament cells, keratinocytes, epithelial cells, endothelial cells, mesenchymal stem cells, and/or embryonic stem cells.

Figure 4:
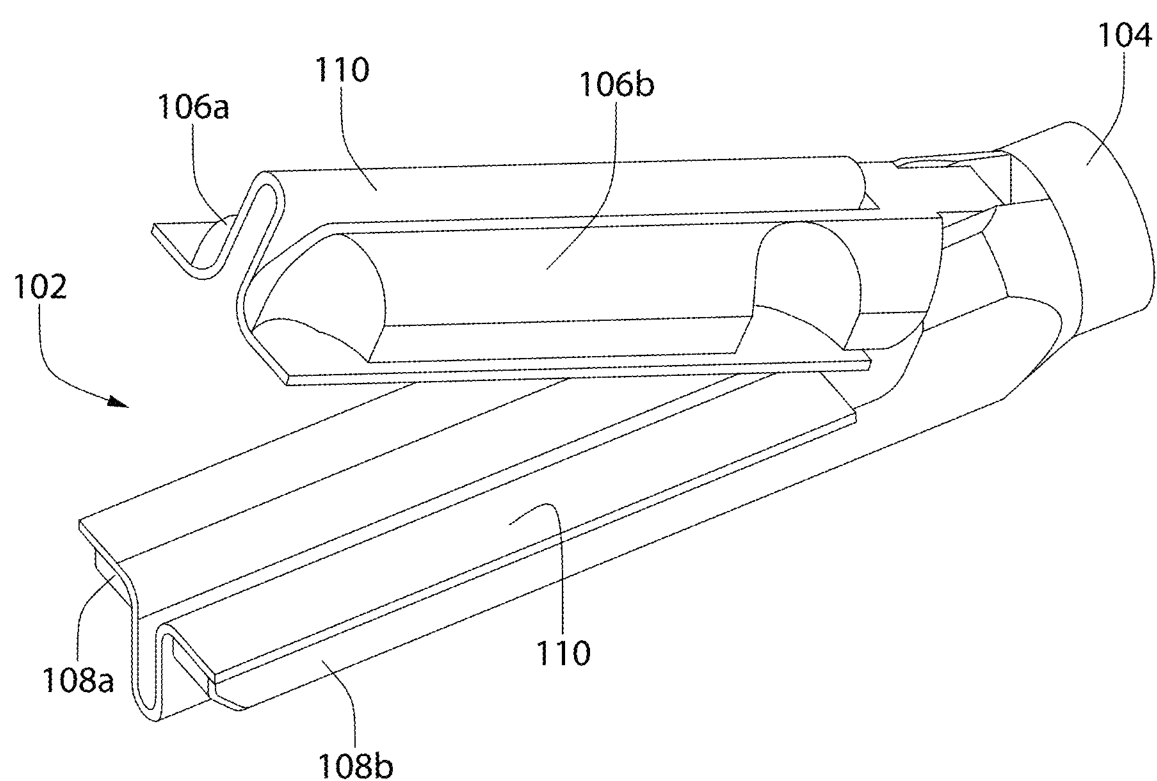
FIG. 4 depicts a magnified perspective view of an expandable grasping end of an exemplary fastener anchoring device.

It should be understood that the several features of the fastener anchoring devices of the present invention can be rearranged or modified without altering their function to accommodate different orientations and configurations. For example, in some embodiments grasper 102 comprises split upper and lower jaws that are laterally expandable to support wide support materials 110. As shown in FIG. 4, a laterally expandable grasper 102 comprises an upper split jaw 106*a* and 106*b* and a lower split jaw 108*a* and 108*b*. Grasper 102 can be laterally expanded and retracted by a mechanical or electronic link extending to the handle of device 100 via shaft 104. Support material 110 is shown preloaded onto grasper 102 in a folded configuration such that grasper 102 can fit through a laparoscopic port for delivery to a target site, whereupon grasper 102 can be laterally expanded to unfold support material 110. While grasper 102 in FIG. 4 is depicted with bifurcated jaws, it should be understood that the jaws of grasper 102 can be split in any suitable manner and into as many parts necessary to load and deliver a support material 110.

In some embodiments, device 100 can further comprise actuatable needles and a suture loading mechanism for suture delivery and suture passing. The needles can be retracted into upper jaw 106, lower jaw 108, or both. The needles can be preloaded with a length of suture thread and actuated with the handle of device 100 to pass the suture through materials held within grasper 102, such as support material 110 and a target site or tissue.

The fastener anchoring devices of the present invention can be made using any suitable method known in the art. The method of making may vary depending on the materials used. For example, components of the device comprising a metal may be milled from a larger block of metal or may be cast from molten metal. Likewise, components of the device substantially comprising a plastic or polymer may be milled from a larger block or injection molded. In some embodiments, the devices may be made using 3D printing or other additive manufacturing techniques commonly used in the art.

Methods of Repairing Soft Tissue

The present invention also provides methods of repairing soft tissue using the fastener anchoring devices described herein. In various embodiments, the soft tissue can be a tendon or a ligament. In some embodiments, the methods are useful in repairing soft tissue to soft tissue, such as a torn tendon or ligament. In some embodiments, the methods are useful in repairing soft tissue to bone, wherein the soft tissue is strengthened prior to anchoring to bone. The methods begin with a step of providing a fastener anchoring device. In some embodiments, the methods comprise a step of selecting a support material to be loaded onto the fastener anchoring device. The support material can be selected based upon the soft tissue in need of repair. For example, support material composition may be selected to match the composition of an underlying soft tissue and may be embedded with factors and populations of cells native to or compatible with an underlying soft tissue. In a following step, a support material is fastened to a soft tissue by grasping the soft tissue with the fastener anchoring device such that the fasteners are inserted into the soft tissue and actuating a retaining band to release the fasteners and support material from the fastener anchoring device. In some embodiments, the support material is fastened to a single surface of a soft tissue. In some embodiments, the support material wraps around an edge of the soft tissue and is fastened to both an upper surface and a lower surface of the soft tissue. After release, the soft tissue is supplemented and strengthened with the support material and can begin healing. In some embodiments, the methods further comprise steps of anchoring the soft tissue supplemented with support material to bone, wherein one or more anchors are driven into an adjacent bone and suture threads are passed through the soft tissue and support material and tied to the one or more anchors.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A fastener anchoring device, comprising:

a shaft connected to a handle and a grasper;

wherein the grasper comprises an upper jaw connected to a lower jaw;

wherein at least one of the upper jaw and lower jaw comprises at least one fastener slot adjacent to a channel having a slideable retaining band, the retaining band having a width that partially occludes the at least one fastener slot; and wherein a fastener having a fastener head is positioned in each fastener slot of the at least one fastener slot such that the fastener protrudes from each fastener slot of the at least one fastener slot and the retaining band holds the fastener head within each fastener slot of the at least one fastener slot.

2. The device of claim 1, wherein sliding the retaining band away from the at least one fastener slot releases the fastener positioned within the at least one fastener slot.

3. The device of claim 1, wherein the retaining band comprises at least one release slot alignable with a fastener slot of the at least one fastener slot to complete an aperture sized to match the fastener head.

4. The device of claim 3, wherein sliding the retaining band aligns the at least one release slot with the at least one fastener slot and releases the fastener positioned within the at least one fastener slot.

5. The device of claim 1, wherein the fastener is selected from the group consisting of: staples, barbs, pins, hooks, spurs, spikes, and anchors.

6. The device of claim 1, wherein the fastener is biodegradable.

7. The device of claim 1, wherein the fastener is non-biodegradable.

8. The device of claim 1, wherein a support material is preloaded onto the fastener protruding from the upper jaw, the lower jaw, or both.

9. The device of claim 8, wherein the support material is a scaffold.

10. The device of claim 8, wherein the support material is constructed from a synthetic material, a biological material, or both.

11. The device of claim 9, wherein the support material comprises an anisotropic material.

12. The device of claim 9, wherein the support material comprises an isotropic material.

13. The device of claim 10, wherein the synthetic material is selected from the group consisting of: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO), polyorthoesters, and combinations thereof.

14. The device of claim 10, wherein the biological material is selected from the group consisting of: collage, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, proteoglycans, polysaccharides (e.g. cellulose and its derivatives), chitin, chitosan, alginic acids, alginates, and combinations thereof.

15. The device of claim 8, wherein the support material further comprises a factor selected from the group consisting of: epidermal growth factor (EGF), platelet derived growth factor (PDGF), basic fibroblast growth factor (bFGF), transforming growth factor-β (TGF-β), tissue inhibitors of metalloproteinases (TIMP), antibiotics, bacteriocides, fungicides, silver-containing agents, analgesics, nitric oxide releasing compounds, and combinations thereof.

16. The device of claim 8, wherein the support material further comprises a population of cells selected from the group consisting of: fibroblasts, osteoblasts, tenoblasts, tenocytes, ligament cells, keratinocytes, epithelial cells, endothelial cells, mesenchymal stem cells, embryonic stem cells, and combinations thereof.

17. The device of claim 1, wherein the upper jaw and the lower jaw are each laterally expandable.

18. The device of claim 17, wherein a support material is preloaded onto the fastener protruding from the laterally expandable upper jaw, the laterally expandable lower jaw, or both.

* * * * *